(12) United States Patent
Pavlik et al.

(10) Patent No.: US 6,936,030 B1
(45) Date of Patent: Aug. 30, 2005

(54) INJECTOR SYSTEMS INCORPORATING A BASE UNIT ATTACHED TO A SURFACE

(75) Inventors: P. Eric Pavlik, Natrona Heights, PA (US); Edward J. Ramsey, Verona, PA (US)

(73) Assignee: Medrad, Inc., Indianola, PA (US)

( * ) Notice: Subject to any disclaimer, the term of this patent is extended or adjusted under 35 U.S.C. 154(b) by 200 days.

(21) Appl. No.: 10/006,586

(22) Filed: Nov. 5, 2001

Related U.S. Application Data

(60) Provisional application No. 60/247,356, filed on Nov. 8, 2000.

(51) Int. Cl.[7] .......................... A61M 37/00; A61B 6/00; A47F 7/19; A47B 96/06; F16M 13/00
(52) U.S. Cl. ................. 604/154; 600/432; 128/DIG. 1; 128/DIG. 12; 211/85.13; 248/218.4; 248/518; 248/535; 248/539
(58) Field of Search .......................... 604/93.01, 118, 604/121, 131, 152, 154, 181, 187, 533, 534, 604/535; 600/431, 432; 128/DIG. 1, DIG. 12; 211/85.13; 248/218.4, 311.2, 518, 535, 539

(56) References Cited

U.S. PATENT DOCUMENTS

| | | | | |
|---|---|---|---|---|
| 5,176,343 A | * | 1/1993 | Cheney et al. | 248/51 |
| 5,494,036 A | * | 2/1996 | Uber et al. | 600/432 |
| 5,588,166 A | * | 12/1996 | Burnett | 5/503.1 |
| 5,829,723 A | * | 11/1998 | Brunner et al. | 248/222.13 |
| 5,925,022 A | * | 7/1999 | Battiato et al. | 604/208 |

* cited by examiner

*Primary Examiner*—Nicholas D. Lucchesi
*Assistant Examiner*—Mark K. Han
(74) *Attorney, Agent, or Firm*—Gregory L. Bradley; Henry E. Bartony, Jr.

(57) ABSTRACT

An injector system for use in delivering a fluid to a patient in a medical procedure includes an injection head unit having at least one pressurizing member. The pressurizing member is in communicative connection with a remote power source via at least one non-rigid drive connection. A connecting member is attached to the injection head unit. The injector system further includes a base unit having a base member that is attachable to a surface and a support member to which the connecting member is attachable.

20 Claims, 5 Drawing Sheets

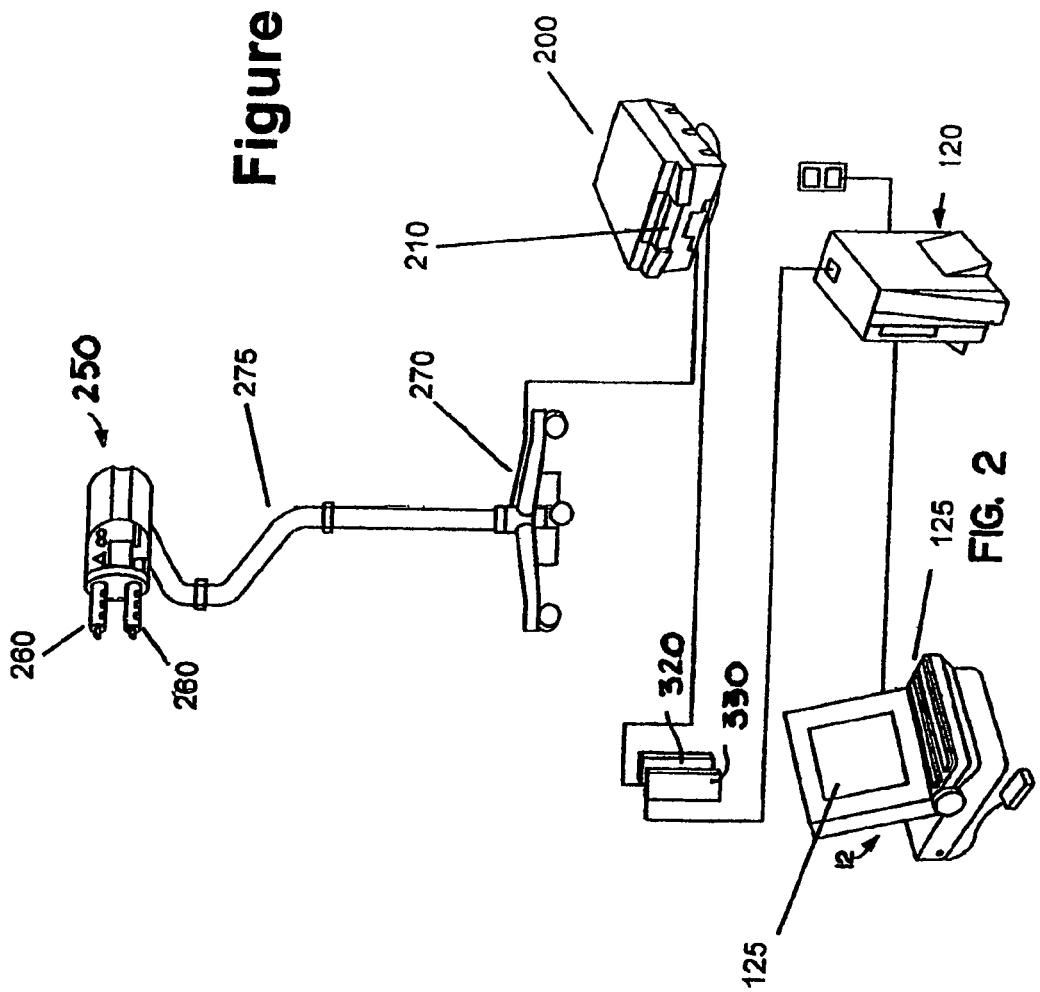

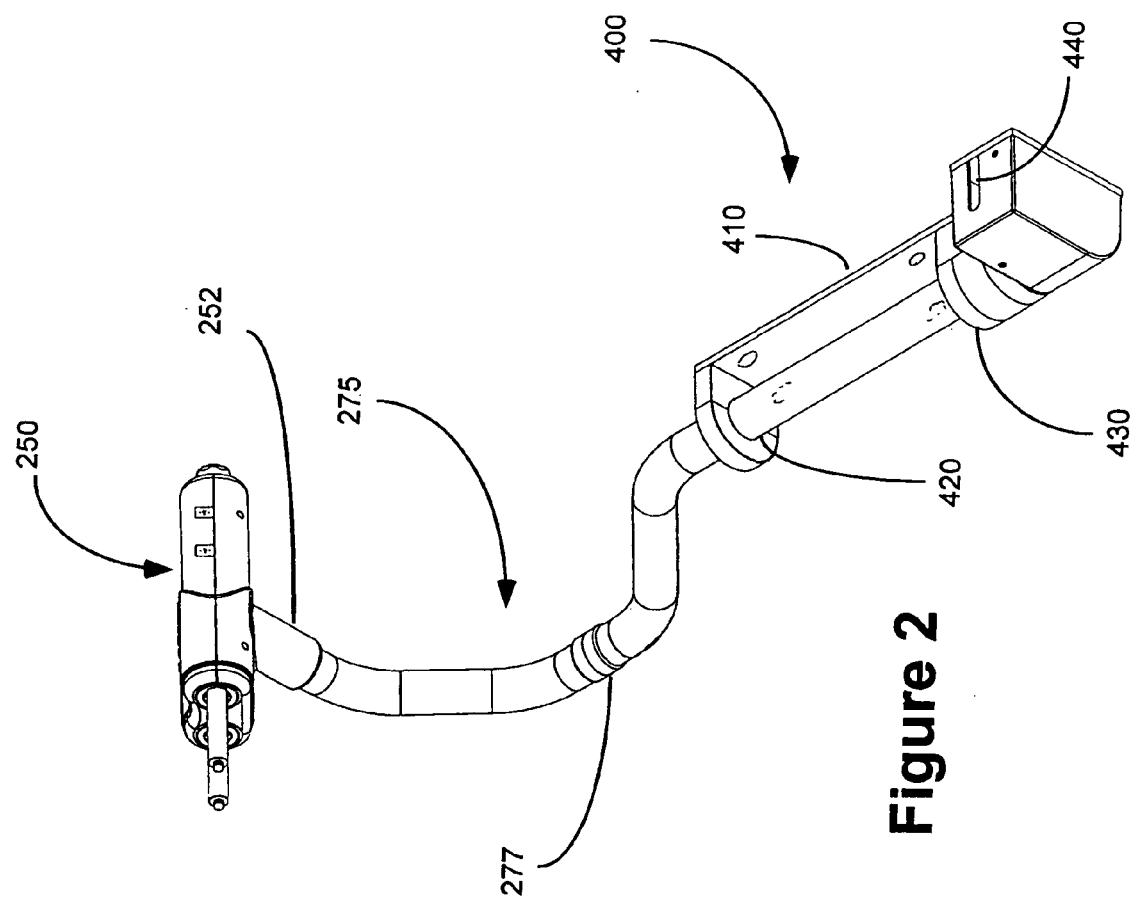

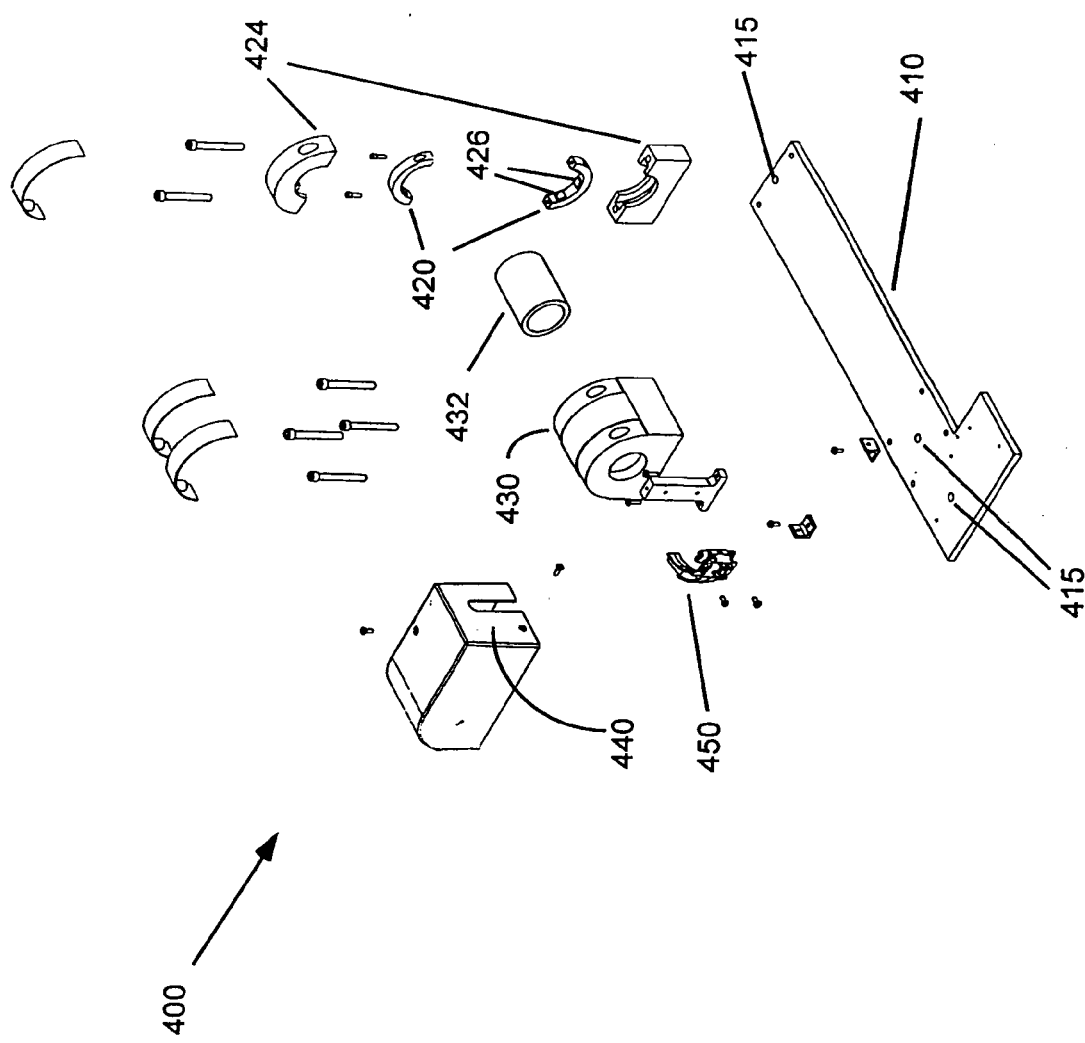

INJECTOR SYSTEMS INCORPORATING A BASE UNIT ATTACHED TO A SURFACE

CROSS REFERENCE TO RELATED APPLICATION

This application claims the benefit of U.S. Provisional Application Ser. No. 60/247,356, entitled POWERED INJECTOR SYSTEMS, filed on Nov. 8, 2000, the disclosure of which is incorporated herein by reference.

BACKGROUND OF THE INVENTION

The present invention relates to powered injector systems and methods and, more particularly, to powered injector systems and methods that facilitate positioning of the powered injectors in medical injection procedures.

In many medical diagnostic and therapeutic procedures, a physician or other person injects a patient with a fluid. In recent years, a number of injector-actuated syringes and powered injectors for pressurized injection of fluids such as contrast media have been developed for use in procedures such as angiography, computed tomography, ultrasound and NMR/MRI. In general, these powered injectors are designed to deliver a preset amount of contrast media at a preset flow rate.

In many situations in which a powered injector is used, space is limited and there are difficulties in properly placing the powered injector for optimal fluid delivery to the patient as well as for optimal movement of medical personnel working around the powered injector. Ideally, the injection head of the powered injector is placed relatively close to the patient without obstructing the movement of the medical personnel in the room.

The problem of injector positioning is typically heightened in a magnetic resonance imaging (MRI) environment. In general, MRI systems require isolation from external sources of electromagnetic noise to optimize image quality. Conventional MRI systems, therefore, typically include some form of electromagnetic isolation shield or barrier. Most often, a room enclosed by copper sheeting or conductive mesh material isolates or shields the imaging system from undesirable sources of electromagnetic radiation, including the electromagnetic noise inherent in the atmosphere. Typically, theses shielded rooms are limited in size. Moreover, mobile MRI systems have recently been developed that are housed in even smaller, mobile units.

It is very desirable to develop injectors, injector systems and methods to facilitate injection proceedings.

SUMMARY OF THE INVENTION

In one aspect, the present invention provides an injector system for use in delivering a fluid to a patient in a medical procedure. The injector system includes an injection head unit including at least one pressurizing member. A connecting member is attached to the injection head unit. The injector system further includes a base unit having a base member that is attachable to a surface and a support member to which the connecting member is attachable. In a dependent aspect, the pressurizing member is in communicative connection with a remote power source via at least one non-rigid drive connection.

Preferably, the connecting member is removably attachable to the support member. In one embodiment, the connecting member is rotatable within the support member. The support member can, for example, include at least one bushing member within which the connecting member can rotate. The connecting member can, for example, be generally cylindrical and include a passage therethrough, through which the non-rigid drive connection is connected to the pressurizing member. The base unit preferably includes a passage or portal through which the non-rigid connection connects to the remote power source.

The present invention also provides a method for delivering fluid to a patient in a medical procedure. The method includes attaching a base unit to a surface, and attaching an injection head unit to the base unit via a connecting member that cooperates with the base unit. The method further includes attaching a pressurizing member in the injection head unit to a power source remote from the injection head and the base unit via at least one non-rigid drive connection.

The present invention further provides a method of adapting an injector system for use in confined spaces. The injector system includes an injection head unit, and a connecting member attached to the head unit at a first end of the connector and attached to a floor stand at a second end of the connecting member. The method includes providing a base unit adapted to be attachable to a surface, and removing the connecting member from attachment with the floor stand so that the second end of the connecting member is attachable to the base unit. In a dependent aspect, the injector system further includes a power source connected to at least one drive member in the injection head unit via at least one non-rigid drive connection.

Numerous other objects and advantages of the present invention will be apparent from the following drawings and detailed description of the invention and its preferred embodiments.

BRIEF DESCRIPTION OF THE DRAWINGS

FIGS. 1A and 1B illustrate an embodiment of a currently available injector system used in MRI procedures.

FIG. 2 illustrates a perspective view of one embodiment of an injector system of the present invention.

FIG. 4 illustrates a perspective view of the base unit of FIGS. 2 and 3 in a disassembled state.

DETAILED DESCRIPTION OF THE INVENTION

One embodiment of the present invention is described below for use in an MRI environment. The injectors systems and methods of the present invention are not limited, however, to use in MRI procedures. For example, injectors used in CT, ultrasound and angiographic imaging procedures can be used with and incorporated into the present invention.

Figure 1A:
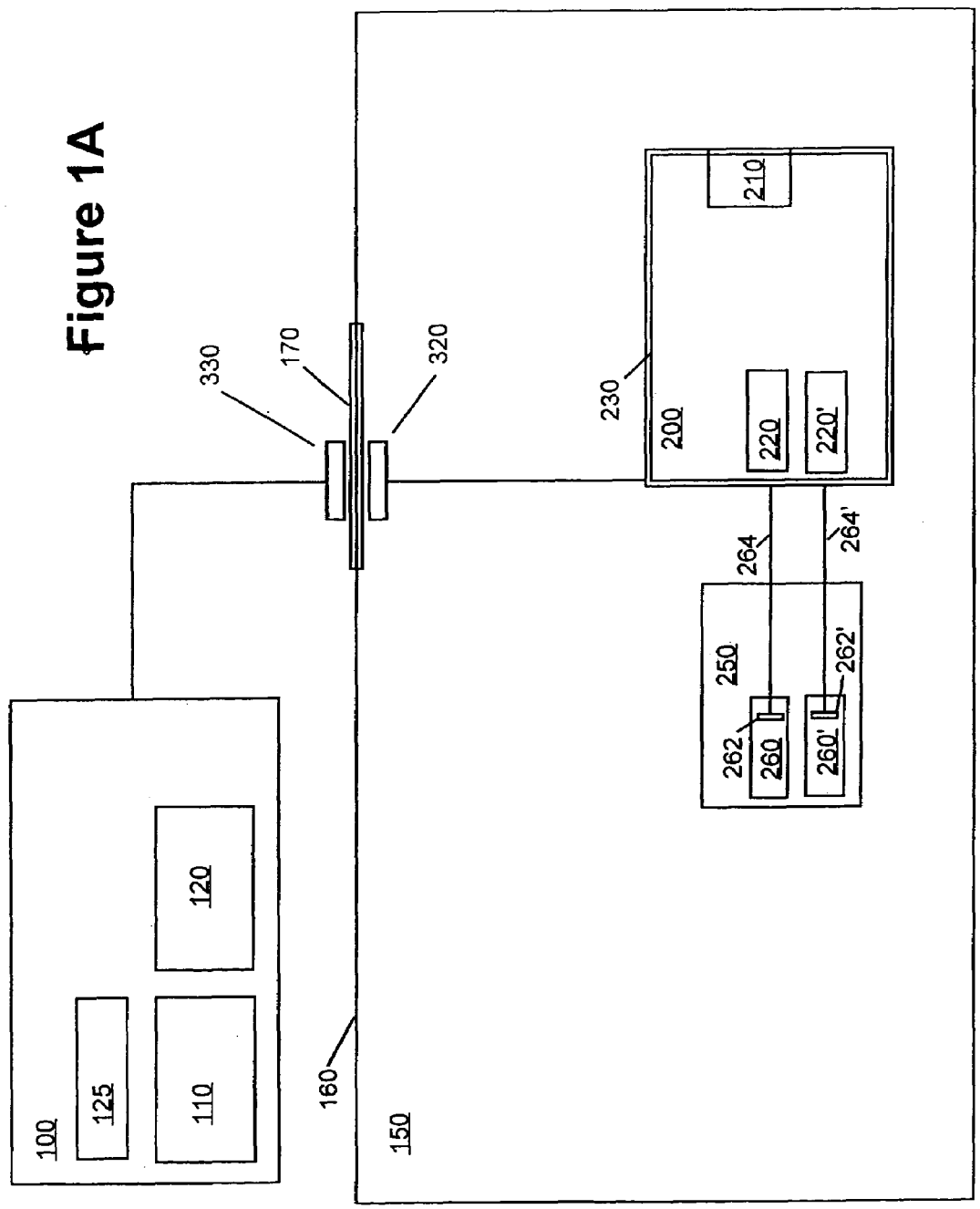

FIGS. 1A and 1B illustrate a Spectris® injector system for use in a magnetic resonance imaging environment, which is currently available from Medrad, Inc. of Indianola, Pa., the Assignee of the present application. One embodiment of the injector system of FIGS. 1A and 1B is described in U.S. Pat. No. 5,494,036, assigned to the Assignee of the present invention, the disclosure of which is incorporated herein by reference. The system includes an external system controller 100 that preferably includes a processing unit 110 (for example, a digital microcomputer), a battery charger 120 and an operator interface 125 (including, for example a data entry unit 125' and a display 125"). System controller 100 is located outside of a shielded area such as an imaging room 150 that is shielded from electromagnetic interference by, for example, a shield 160. Electromagnetic isolation can, for example, be achieved by completely enclosing the room with copper sheet material or some other suitable, conductive layer such as wire mesh.

Shielded imaging room 150 preferably includes a patient viewing window 170 in shield 160 to allow an observer and/or operator to view the room without breaching electromagnetic shield 160. Window 170 can, for example, be formed by sandwiching a wire mesh material (not shown) between sheets of glass or by coating the window with a thin coating of conductive material such as gold (not shown) to maintain the continuity of electromagnetic shield 160.

The system also includes a contrast media injection control unit 200 located within shielded imaging room 150. Injection control unit 200 is preferably powered by a rechargeable battery 210. Injection control unit 200 preferably includes control circuitry which controls electric motors 220 and 220', which are preferably located within injection control unit 200. Injection control unit 200 is preferably contained within an electromagnetic shield 230 to reduce or eliminate any undesired electromagnetic radiation generated by electric motors 220 and 220' from interfering with the magnetic field used to generate the magnetic resonance image.

Separation of the electric motors from the injection head 250, as well as the additional electromagnetic shielding, results in improved system performance and improved overall image quality. Injection control unit 200 can be separated (for example, by ten to fifteen feet) from injection head unit 250, which is typically placed near the patient. As illustrated in FIG. 1B, injection head unit 250 is mounted on a mobile base unit 270 via a connecting member 275.

Injection head unit 250 is preferably located in close proximity to the patient to decrease the distance that the contrast media fluid must travel from the contrast media from syringes 260 and 260' (or other fluid chambers) connected to injection head unit 250. Injection head unit 250 further includes drive members 262 and 262' such as pistons that act to pressurize the contents of syringes 260 and 260', respectively, for injection into the patient. Drive members 262 and 262' are preferably connected to electric motors 220 and 220', respectively, in injection control unit 200 by a non-rigid connection such as by flexible mechanical drive shafts 264 and 264', respectively. Drive shafts 264 and 264' are preferably made from a nonferrous metal such as hard brass.

For control of injection head unit 250 by system controller 100, communication must be maintained between system controller 100 and injection control unit 200. For example, injector control unit 200 can be in communication with a communication unit 320. Likewise, control system 100 can be in communication with a communication unit 330. Communication units 320, 330 can, for example, communicate across viewing window 170 using light energy as disclosed in U.S. Pat. No. 5,494,036.

Figure 3:
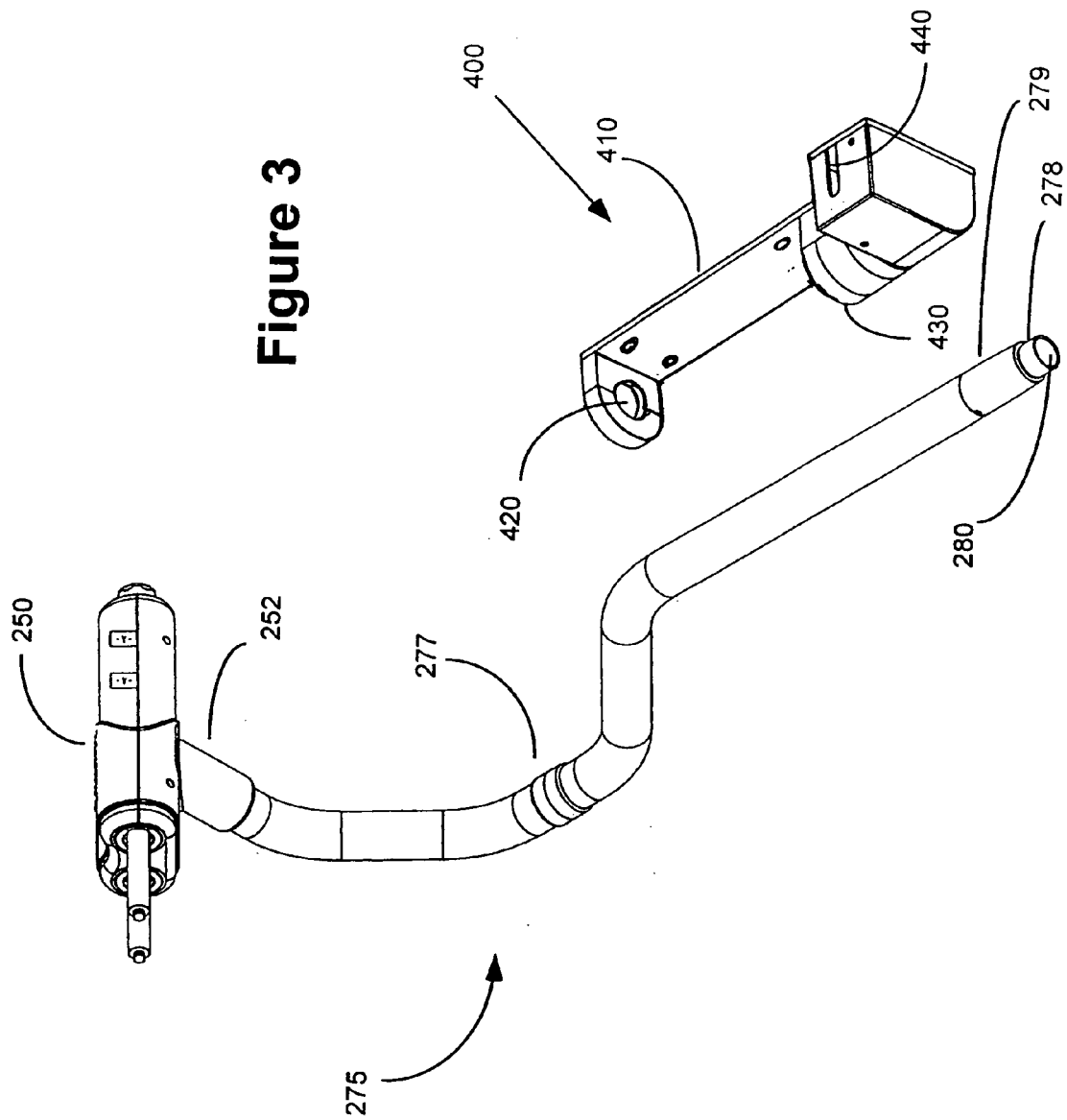
FIG. 3 illustrates a perspective view of the injection head unit and base unit of FIG. 2 in an disconnected state.

Although mobile base unit 270 provides substantial mobility to injection head unit 250 and enables placement thereof in the vicinity of the patient in many settings, lack of space in other settings can limit the mobility of both mobile base unit 270 and the medical personnel working around mobile base unit 270. FIGS. 2 through 4 illustrate an embodiment of the present invention in which connecting member 275 cooperates with a stationary base unit 400 to enable positioning of injection head unit 250 in the vicinity of a patient in, for example, MRI rooms of little space, without substantially obstructing the mobility of medical personnel. In one aspect, base unit 400 includes an attachment member or plate 410 that is attachable to, for example, a wall, a ceiling, a post or another surface (either generally flat or contoured) of a room via, for example, screws, adhesive or other attachment means or members. Screws or other attachment members can, for example, pass through holes 415 (see FIG. 4) in attachment plate 410. Preferably, holes 415 are hidden from view/access when base unit 400 is fully assembled to reduce the likelihood that the attachment members will become loosened or detached and to enhance the appearance of base unit 400.

Base unit 400 further preferably includes a support mechanism for removably retaining connecting member 275 therein. In the embodiment of FIGS. 2 and 3, connecting member 275 includes a number of connected sections of hollow tubing that are preferably attached (for example, via at least one coupler 277) so that they can be rotated relative to each other to provide mobility to injection head unit 250. Likewise, connecting member 275 is preferably rotatably attached to in injection head unit 250 via, for example, a collar 252. Connecting member 275 is preferably releasably attachable to base unit 400 via, for example, at least one bushing 420 so that connecting member 275 is rotatable within base unit 400. As illustrated in FIG. 4, bushing 420 includes two sections that are rotatably housed in a housing 424. Bushing 420 preferably includes an adapter mechanism to enable bushing 420 to accept and retain connecting members 275 of differing size and/or shape without introducing excessive play into the system. For example, bushing 420 can include biasing members or pads 426 (for example, spring-loaded abutment members or elastomeric pads) that act to securely grasp connecting member 275. The compressibility of such members or pads 426 enables use of connecting members 275 having, for example, variations in the diameter thereof without introducing play into the system. Housing 424 attaches to attachment plate 410 via attachment members as known in the art (for example, screws) and can cover one or more of base plate attachment holes 415 when base 400 is assembled as described above.

In the embodiment of FIGS. 2 through 4, base unit 400 also includes a second bushing unit or bushing housing 430 that includes a bushing (not shown) similar to bushing 420. The bushing of bushing unit 430 cooperates with a distal end of connecting member 275 to rotatably attach connecting member 275 to base unit 400. Bushing unit 430 can, for example, include a retainer as known in the art (for example, an adapter nut) that rotatably and removably attaches connecting member 275 to base unit 400 during use thereof via, for example, a threaded end 278 on connecting member 275. In the embodiment of FIG. 4, bushing unit 430 includes an adapter 432 having a tapered inner bore that matches a tapered portion 279 of connecting member 275. The outer surface of adapter 432 is generally cylindrical and rotatably seats within bushing unit 430.

Base unit 400 further preferably includes a passage or portal 440 to allow a power source to pass therethrough and subsequently through connecting member 275 (via, for example, passage 280 therein) to provide power to drive members 262 and 262' as discussed above. The power source can, for example, be flexible mechanical drive shafts 264 and 264 as discussed above. In the case that one or more flexible mechanical drive shafts are used, base unit 400 preferably includes at least one guide 450 that prevents excessive bending of the flexible mechanical drive shaft(s) in the area(s) in which such shafts change direction. In one embodiment, for example, a guide with a minimum radius of approximately three inches was used. Alternatively, other power sources such as hydraulic or pneumatic lines can be used as a source of power.

Current injector systems in which the injection head unit is connected to a remote power source via a non-rigid connection (such as the Spectris® injector system described above) are easily retrofitted to practice the present invention. For example, the injection head unit and connecting member of the existing injector system (for example, the Spectris® injector system) are preferably directly usable with base unit 400 of the present invention with little or no modification thereof. In that regard, bushing 420, the bushing of bushing unit 430 and adapter 432 are preferably sized and generally adapted to accommodate the connecting member of the existing injector system. Likewise, the retaining member (not shown) of base unit 400 is also adapted to accept the connecting member of the exiting injector system. Nevertheless, it is specifically contemplated that conventional injector systems having a power source that is not remotely connected to a drive mechanism via a non-rigid connection can also be used with the present invention. Examples of such injector systems are the EnVision CT™ and Medrad Vistron CT® injectors provided by Medrad, Inc., the Assignee of the present application.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations which come within the meaning and range of equivalency of the claims are to be embraced within their scope.

What is claimed is:

1. An injector system comprising:
   an injection head unit comprising at least one pressurizing member;
   a stationary base unit adapted to be attached to a surface other than a surface of the injector system; and
   a connecting member connected to the injection head unit and the stationary base unit.

2. The injector system of claim 1 wherein the connecting member is removably connected to the stationary base unit.

3. The injector system of claim 1 wherein the connecting member is movably connected to the stationary base unit.

4. The injector system of claim 3 wherein the connecting member is rotatably connected to the stationary base unit.

5. The injector system of claim 4 wherein the base unit comprises a bushing member and the connecting member is rotatably connected to the base unit via cooperation with the bushing member, the bushing member comprising an adapter to accept different connecting members.

6. The injector system of claim 1 wherein the pressurizing member is connected to a remote power source via at least one non-rigid drive connection and the connecting member is generally cylindrical and defines a passage therethrough, the non-rigid drive connection being connected to the pressurizing member via the passage in the connecting member.

7. The injector system of claim 6 wherein the base unit defines a portal through which the non-rigid connection passes to connect to the remote power source.

8. The injector system of claim 1 wherein the connecting member is movably connected to the injection head unit.

9. The injector system of claim 1 wherein the connecting member comprises two or more connected sections.

10. The injector system of claim 9 wherein the two or more connected sections are adapted to be rotated relative to each other.

11. The injector system of claim 9, further comprising a coupler for attaching the two or more connected sections to each other.

12. The injector system of claim 1 wherein the connecting member is rotatably connected to the injection head unit and the stationary base unit.

13. The injector system of claim 1 wherein the surface is a wall, a ceiling or a post.

14. The injector system of claim 1 wherein the stationary base unit is attached to the surface by means of fasteners or adhesives.

15. The injector system of claim 1 wherein the at least one pressurizing member comprises a drive mechanism.

16. A method for delivering fluid to a patient in a medical procedure, the method comprising:
    attaching a base unit to a surface other than a surface of the injector system;
    attaching an injection head unit to the base unit via a connecting member that cooperates with the base unit; and
    activating a pressurizing member in the injection head unit to deliver fluid to the patient.

17. The method of claim 16 wherein the pressurizing member in the injection head unit is connected to a power source by means of a non-rigid drive connection.

18. A method of adapting an injector system for use in confined spaces, the injector system comprising an injection head unit, and a connecting member attached to the head unit at a first end of the connector and attached to a mobile floor stand at a second end of the connecting member, the method comprising:
    attaching a base unit to a surface other than a surface of the injector system;
    removing the connecting member from attachment with the mobile floor stand; and
    removably connecting the second end of the connecting member to the base unit.

19. The method of claim 18 wherein the injector system further comprises a power source connected to at least one drive member in the injection head unit via at least one non-rigid drive connection.

20. The method of claim 18, further comprising:
    removing the second end of the connecting member from the base unit; and
    reattaching the second end of the connecting member to the mobile floor stand.

* * * * *